United States Patent
Ikehara et al.

(10) Patent No.: US 12,216,045 B2
(45) Date of Patent: Feb. 4, 2025

(54) MEASUREMENT APPARATUS

(71) Applicants: Shimadzu Corporation, Kyoto (JP); National University Corporation Tokai National Higher Education and Research System, Nagoya (JP)

(72) Inventors: Tatsuya Ikehara, Kyoto (JP); Tetsuo Furumiya, Kyoto (JP); Koji Tojo, Kyoto (JP); Hideki Tomita, Nagoya (JP)

(73) Assignees: SHIMADZU CORPORATION, Kyoto (JP); National University Corporation Tokai National Higher Education and Research System, Nagoya (JP)

( * ) Notice: Subject to any disclaimer, the term of this patent is extended or adjusted under 35 U.S.C. 154(b) by 103 days.

(21) Appl. No.: 18/101,644

(22) Filed: Jan. 26, 2023

(65) Prior Publication Data
US 2023/0236116 A1    Jul. 27, 2023

(30) Foreign Application Priority Data
Jan. 27, 2022    (JP) .................................. 2022-010889

(51) Int. Cl.
*G01N 21/31* (2006.01)
*G01N 33/00* (2006.01)

(52) U.S. Cl.
CPC ......... *G01N 21/31* (2013.01); *G01N 33/0027* (2013.01); *G01N 2201/02* (2013.01); *G01N 2201/0636* (2013.01)

(58) Field of Classification Search
CPC ....... G01N 2021/391; G01N 2021/399; G01N 21/0332; G01N 21/31; G01N 21/39; G01N 2201/02; G01N 2201/0636; G01N 33/0027
See application file for complete search history.

(56) References Cited

U.S. PATENT DOCUMENTS

2016/0349177 A1* 12/2016 Iguchi ................ G01N 21/3504

OTHER PUBLICATIONS

Alan Daniel McCartt, "Development of a low-temperature cavity Ring-Down Spectrometer for the detection of CarBon-14", Stanford University, Jul. 2014, from https://www.proquest.com/openview/dd87a1d8b13db79fd5698d9b68234645/1.pdf?pq-origsite=gscholar&cbl=51922&diss=y.
Kate Dennis, "Picarro Product Portfolio Update: The new frontier in Cavity Ring-Down Spectroscopy", ASITA Conference, University of California-Davis Jun. 17, 2014, from https://www.picarro.com/sites/default/files/Dennis_ProductPortfolio_ASITA2014_public.pdf.

* cited by examiner

*Primary Examiner* — Hina F Ayub
(74) *Attorney, Agent, or Firm* — Muir Patent Law, PLLC

(57) ABSTRACT

A gas measurement apparatus includes an optical resonator that resonates light, a light source that generates light for irradiation of the optical resonator, and a photodetector that detects light taken out of the optical resonator. The optical resonator includes a plurality of mirrors, a holding member, a hollow tubular member, a hollow tubular member, and a temperature adjustment instrument. The holding member is lower in thermal expansion coefficient than the hollow tubular member. The hollow tubular member includes a portion higher in thermal conductivity than the holding member and a bellows higher in elasticity than a first portion. The hollow tubular member is equal to or higher than the hollow tubular member in thermal conductivity, and is provided as far as positions of the plurality of mirrors on an inner side of the bellows.

7 Claims, 5 Drawing Sheets

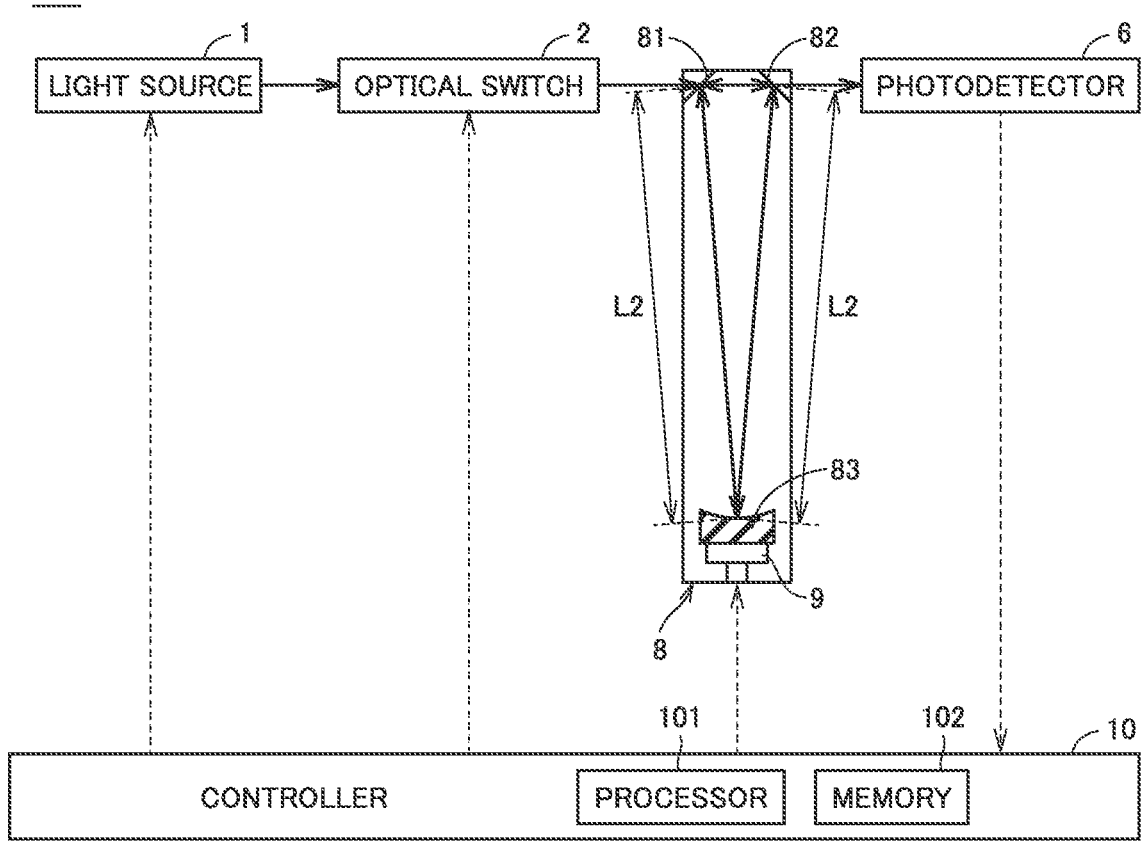

MEASUREMENT APPARATUS

BACKGROUND OF THE INVENTION

Field of the Invention

The present disclosure relates to a measurement apparatus including an optical resonator.

Description of the Background Art

A gas measurement apparatus based on measurement principles such as gas absorption spectroscopy has widely been used in measurement of an environmental pollutant in air. The gas measurement apparatus irradiates measurement target gas with light and quantifies a substance contained in that gas based on intensity of light absorbed at a frequency as high as a resonant frequency of the substance.

For example, in measurement of volatile organic compounds (VOC) or an extremely small amount of gas (carbon monoxide, an isotope of carbon dioxide, or the like) contained in measurement target gas, the gas measurement apparatus should measure measurement target gas with the use of an optical resonator for improving detection sensitivity. For example, "Development of a low-temperature cavity Ring-Down Spectrometer for the detection of Car-Bon-14," McCartt, Stanford University, July 2014 discloses a gas measurement apparatus including an optical resonator.

SUMMARY OF THE INVENTION

The optical resonator can increase an effective optical path length that can be used for measurement of gas to the order of kilometers by reflecting light between at least two high-reflection mirrors. Therefore, great deformation of the optical resonator due to heat significantly affects detection sensitivity of the gas measurement apparatus. Then, the optical resonator may be composed of a material low in thermal expansion coefficient (for example, an Invar® alloy or ultra-low-expansion glass).

When the optical resonator is composed of a material low in thermal expansion coefficient, however, long time is required to increase or decrease a temperature in the optical resonator to a target temperature because of the low thermal conductivity of the material. Furthermore, when the optical resonator is composed of the material low in thermal conductivity, a temperature distribution in the optical resonator tends to be uneven. Such an uneven temperature distribution becomes a factor for a detection error in measurement of gas with the gas measurement apparatus. In addition, the material low in thermal expansion coefficient is difficult-to-machine and expensive.

The present disclosure was made to solve the problem above, and an object of the present disclosure is to provide a measurement apparatus suitable for measurement with a temperature in an optical resonator being increased or decreased to a target temperature.

A measurement apparatus according to an aspect of the present disclosure includes an optical resonator that resonates light, a light source that generates light for irradiation of the optical resonator, and a photodetector that detects light taken out of the optical resonator. The optical resonator includes a plurality of mirrors, a holder that holds the plurality of mirrors, a first tubular portion including opposing ends in contact with the holder, the first tubular portion defining a space where the plurality of mirrors are accommodated, a second tubular portion provided in the inside of the first tubular portion along the first tubular portion, and a temperature adjustment portion that adjusts a temperature in the inside of the first tubular portion. The holder is composed of a material lower in thermal expansion coefficient than the first tubular portion and the first tubular portion includes a first portion composed of a material higher in thermal conductivity than the holder and a second portion higher in elasticity than the first portion. The second tubular portion is composed of a material equal to or higher than the first portion in thermal conductivity and provided as far as positions of the plurality of mirrors on an inner side of the second portion.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 5 is a block diagram showing an overall configuration of a gas measurement apparatus according to another modification.

DESCRIPTION OF THE PREFERRED EMBODIMENTS

Figure 1:
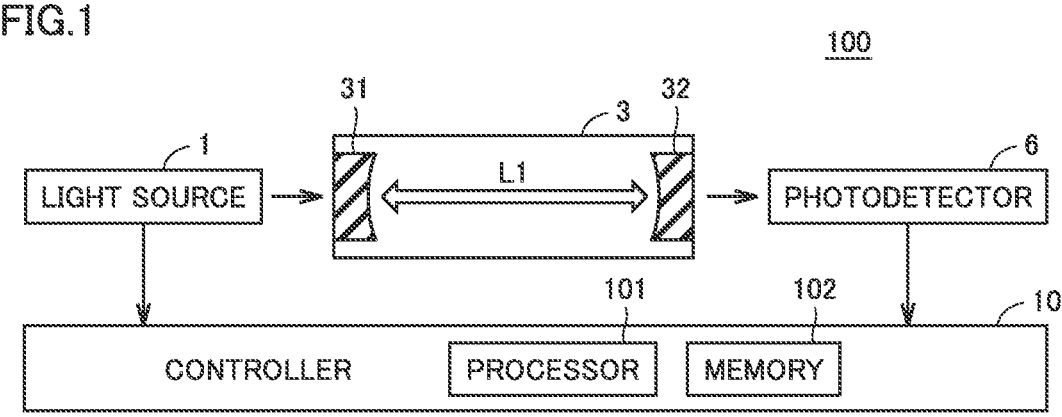
FIG. 1 is a block diagram showing an overall configuration of a gas measurement apparatus according to an embodiment.

An embodiment of the present disclosure will be described below in detail with reference to the drawings. The same or corresponding elements in the drawings have the same reference characters allotted and description thereof will not be repeated.

EMBODIMENT

<Configuration of Measurement Apparatus>

FIG. 1 is a block diagram schematically showing an overall configuration of a gas measurement apparatus 100 according to an embodiment. Gas measurement apparatus 100 shown in FIG. 1 measures with an optical resonator 3, light absorption by a target component contained in gas (sample gas) which is a measurement target. Gas measurement apparatus 100 includes a light source 1 which is a laser light source, optical resonator 3, a photodetector 6, and a controller 10.

Light source 1 emits laser beams for irradiation of light resonator 3. Light source 1 is variable in oscillation frequency of laser beams in accordance with an instruction from controller 10. For example, light source 1 is a laser light source of quantum cascade laser (QCL) and emits mid-infrared laser beams (around a wavelength of 5 μm). Controller 10 can change a drive current to light source 1 to change the oscillation frequency of laser beams.

Optical resonator 3 is a container in which measurement target sample gas can be sealed, and it is, for example, in a hollow tubular shape. Optical resonator 3 is provided with an introduction pipe 41 for introduction of sample gas before start of measurement, an electromagnetic valve 42 provided in introduction pipe 41, a discharge pipe 43 for discharge of sample gas after end of measurement, and an electromagnetic valve 44 provided in discharge pipe 43 (see FIG. 2). Each time measurement is conducted with gas measurement apparatus 100, electromagnetic valves 42 and 44 are opened and sample gas to be measured is sealed in optical resonator 3 through introduction pipe 41, and after measurement, electromagnetic valves 42 and 44 are opened and sample gas subjected to measurement is discharged from optical resonator 3 through discharge pipe 43.

Optical resonator 3 is provided between light source 1 and photodetector 6. Optical resonator 3 includes a pair of mirrors 31 and 32. Mirrors 31 and 32 are arranged as being opposed to each other so as to reflect light therebetween in the inside of optical resonator 3. A mirror high in reflectivity (for example, around 99.98%) is preferably adopted as each of mirrors 31 and 32 such that light that leaks to the outside of optical resonator 3 is extremely weak.

In the present embodiment, a resonator length L1 of optical resonator 3 is defined as a distance between mirror 31 and mirror 32 in a direction of connection of mirror 31 and mirror 32 to each other (a direction of an optical axis). Resonator length L1 is set, for example, to several ten centimeters (approximately 30 cm in this example).

In the example shown in FIG. 1, each of mirrors 31 and 32 is a concave mirror. It is not essential, however, that both of mirrors 31 and 32 are concave mirrors. At least one of mirrors 31 and 32 should only be a concave mirror. For example, one of mirrors 31 and 32 may be a concave mirror and the other may be a plane mirror.

Photodetector 6 is a detector such as a photodiode or an image sensor. Photodetector 6 detects weak transmitted light taken out of mirror 32 and provides a signal (detection signal) indicating a result of detection to controller 10.

Controller 10 includes a processor 101 such as a central processing unit (CPU) or a field-programmable gate array (FPGA), a memory 102 such as a read only memory (ROM) and a random access memory (RAM), and an input and output port (not shown). Controller 10 controls each device included in gas measurement apparatus 100. More specifically, controller 10 provides an instruction for sweep of an oscillation frequency of laser beams to light source 1 or receives a detection signal from photodetector 6. Controller 10 carries out A/D conversion of the detection signal from photodetector 6, and thereafter performs various types of data processing for analyzing information such as a concentration (an absolute concentration) of a target component contained in sample gas based on data resulting from A/D conversion.

Controller 10 may be configured as being divided into at least two units for each function. For example, controller 10 may be divided into a unit that controls each device and a unit that performs various types of data processing.

<Measurement Principles>

Principles in measurement by absorption spectroscopy with the use of optical resonator 3 will briefly be described. In general, for optical resonator 3, there is a resonance condition under which resonance occurs when a frequency of light emitted to optical resonator 3 has a specific frequency. A frequency of laser beams emitted to optical resonator 3 is called a "laser frequency" below. A frequency of light at which resonance in optical resonator 3 may occur is called a "mode frequency."

When the laser frequency is equal to any mode frequency, power of laser beams is stored in optical resonator 3. After power of laser beams is sufficiently stored in optical resonator 3, laser beams emitted to optical resonator 3 are cut off. Light stored in optical resonator 3 before cut-off travels between mirror 31 and mirror 32 a large number of times (normally, several thousand to several ten thousand times). This light gradually attenuates due to absorption by a target component in sample gas while light travels between mirrors 31 and 32. At this time, photodetector 6 detects attenuation of transmitted light that leaks from mirror 32. According to absorption spectroscopy with the use of optical resonator 3, by increasing a distance (an effective optical path length) of passage of light through sample gas with the use of optical resonator 3, light absorption can be detected even though light absorption by the target component is very little.

Controller 10 finds a time constant of attenuation of light based on a detection signal from photodetector 6. An absorption coefficient of a target component at a laser frequency at that time can be calculated from the time constant. An absorption spectrum of the target component can also be generated by sweeping the laser frequency and repeating similar measurement. Furthermore, a concentration of the target component can be calculated from the absorption coefficient.

<Optical Resonator>

Figure 2:
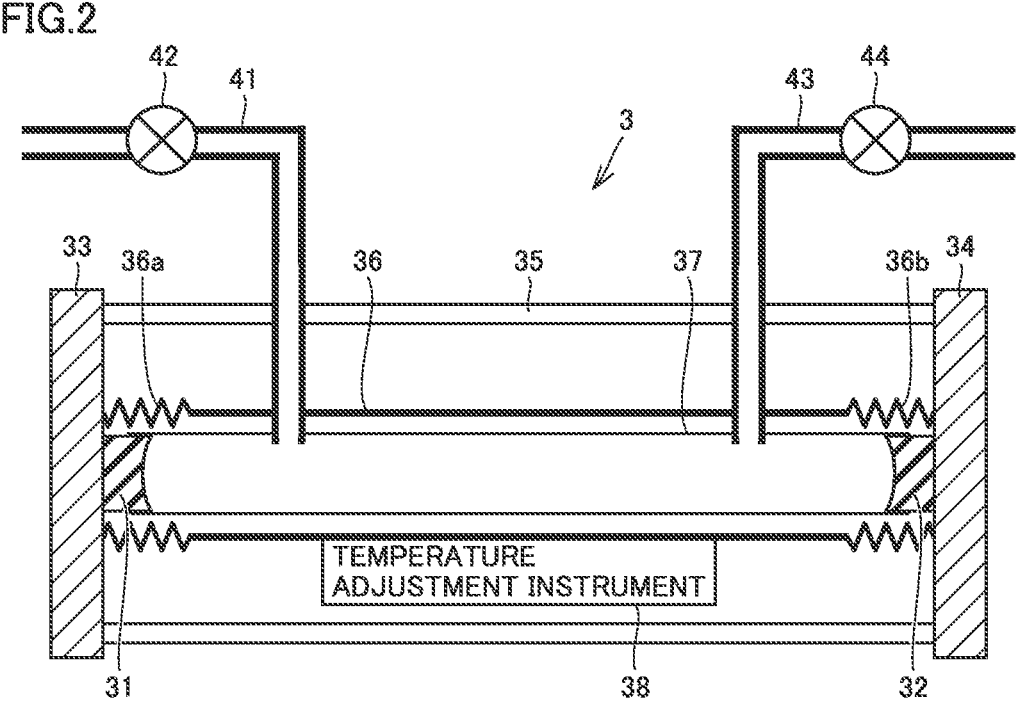
FIG. 2 is a schematic diagram showing a configuration of an optical resonator according to the embodiment.
Figure 3:
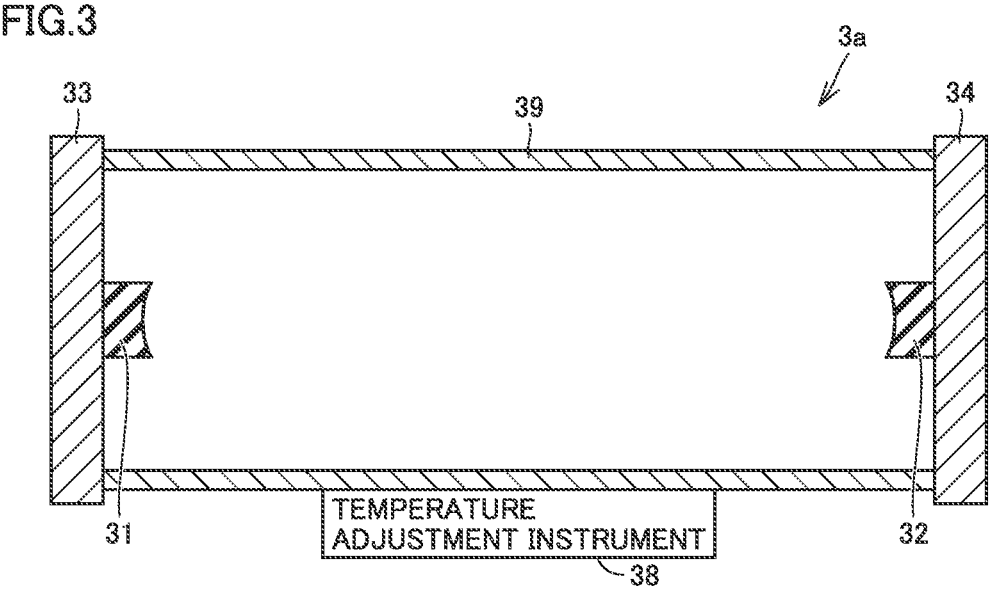
FIG. 3 is a schematic diagram showing a configuration of an optical resonator for comparison.

In order to measure a volatile organic compound or an extremely small amount of gas contained in measurement target gas with gas measurement apparatus 100, a temperature in optical resonator 3 should be low. Therefore, optical resonator 3 is provided with a temperature adjustment instrument that adjusts a temperature therein. FIG. 2 is a schematic diagram showing a configuration of optical resonator 3 according to the embodiment. FIG. 3 is a schematic diagram showing a configuration of an optical resonator 3a for comparison.

Initially, as shown in FIG. 3, optical resonator 3a for comparison is in such a structure that a holding member 33 that holds mirror 31 and a holding member 34 that holds mirror 32 are connected at opposing ends of a hollow tubular member 39. Holding members 33 and 34 and hollow tubular member 39 of optical resonator 3a are composed of a material low in thermal expansion coefficient such that the distance (resonator length L1) between mirror 31 and mirror 32 does not vary.

Furthermore, in order to set a low temperature in the inside, optical resonator 3a is provided with a temperature adjustment instrument 38 to adjust the temperature in optical resonator 3a on a side surface of hollow tubular member 39. Hollow tubular member 39 provided with temperature adjustment instrument 38, however, is composed of the material low in thermal expansion coefficient and hence the thermal conductivity thereof is low. Thus, long time is required to lower the temperature in optical resonator 3a to a target temperature. Furthermore, when optical resonator 3a is composed of the material low in thermal conductivity, a temperature distribution in optical resonator 3a tends to be uneven, which becomes a factor for a detection error in measurement of gas with the gas measurement apparatus.

Then, for optical resonator 3 according to the present embodiment, as shown in FIG. 2, a structure is adopted in which a plurality of rods 35 fix holding members such that the distance (resonator length L1) between holding member 33 (first holder) that holds mirror 31 (first mirror) and holding member 34 (second holder) that holds mirror 32 (second mirror) is constant. Optical resonator 3 is further provided with a hollow tubular member 36 (first tubular portion) that defines a space where mirrors 31 and 32 are accommodated, and ends of hollow tubular member 36 are in contact with holding members 33 and 34. Temperature adjustment instrument 38 that adjusts the temperature in optical resonator 3 is provided on a side surface of hollow tubular member 36.

Optical resonator 3 is in such a structure that at least three rods 35 fix holding members 33 and 34 each in a shape of a flange provided at opposing ends of hollow tubular member 36. Holding members 33 and 34 and rods 35 are composed of a material (for example, an Invar® alloy or ultra-low-expansion glass) lower in thermal expansion coefficient than hollow tubular member 36. Thus, even when the temperature changes, the distance (resonator length L1) between mirror 31 and mirror 32 is less likely to change. Hollow tubular member 36 is composed of a material (for example, aluminum, copper, or the like) higher in thermal conductivity than holding members 33 and 34 and rods 35 such that the inside of optical resonator 3 is readily heated or cooled.

When hollow tubular member 36 is formed only from a portion (first portion) higher in thermal conductivity than holding members 33 and 34 and rods 35, deformation of hollow tubular member 36 caused by temperature change by temperature adjustment instrument 38 may apply force to holding members 33 and 34 and rods 35, which may affect the distance (resonator length L1) between mirror 31 and mirror 32. As shown in FIG. 2, hollow tubular member 36 is provided with bellows 36a and 36b at opposing ends. Bellows 36a and 36b are portions (second portions) higher in elasticity than other portions (first portion) of hollow tubular member 36. Elasticity refers to an amount of deformation caused in a direction of extension of hollow tubular member 36 when tensile stress or compressive stress is applied in the direction of extension, and it can be defined as an elastic compliance constant. Therefore, deformation of the portion (first portion) high in thermal conductivity caused by temperature change by temperature adjustment instrument 38 can be cancelled or lessened by extension and contraction of bellows 36a and 36b (second portions). Optical resonator 3 thus lessens influence on the distance between mirror 31 and mirror 32 held by holding members 33 and 34 and rods 35 while it facilitates temperature adjustment with temperature adjustment instrument 38. Deformation of hollow tubular member 36 may also be caused by thermal fluctuations in the portion where gas is sealed, other than the temperature change by temperature adjustment instrument 38.

Though bellows 36a and 36b are provided at opposing ends of hollow tubular member 36, any one of bellows 36a and 36b alone may be provided in hollow tubular member 36, so long as deformation caused in the portion high in thermal conductivity can be cancelled or lessened. Furthermore, a position where the bellows is provided is not limited to the end of hollow tubular member 36 and the bellows may be provided at another position such as a central portion. Though hollow tubular member 36 may be constructed by making the portion (first portion) high in thermal conductivity and the portion (second portion) of bellows 36a and 36b from different members and then combining them, a part of one member may be worked into a shape of the bellows so that the first portion and the second portion may be constructed as being integrated.

Temperature adjustment instrument 38 is a temperature adjustment portion that adjusts the temperature in the inside of hollow tubular member 36 or 39, and it includes, for example, a heater, a Peltier element, or the like. Controller 10 controls temperature adjustment instrument 38 to set the temperature in the inside of hollow tubular member 36 or 39 to the target temperature.

As described previously, hollow tubular member 36 is not constructed only from the portion (first portion) high in thermal conductivity but includes the portion (second portion) of bellows 36a and 36b. Therefore, the portion of bellows 36a and 36b may function as a thermal resistance and prevent propagation of a quantity of heat from temperature adjustment instrument 38 to the inside of hollow tubular member 36. In other words, by providing the portion of bellows 36a and 36b in hollow tubular member 36, the temperature distribution in hollow tubular member 36 tends to be uneven.

Then, as shown in FIG. 2, optical resonator 3 according to the present embodiment is further provided with a hollow tubular member 37 (second tubular portion) in the inside along hollow tubular member 36. Hollow tubular member 37 is composed of a material (for example, aluminum, copper, or the like) equal to or higher than hollow tubular member 36 in thermal conductivity, and provided as far as positions of mirrors 31 and 32 on the inner side of bellows 36a and 36b. Therefore, hollow tubular member 37 without a thermal resistance can allow propagation of the quantity of heat from temperature adjustment instrument 38 to the entirety of the inside of hollow tubular member 36 including bellows 36a and 36b. In other words, by providing hollow tubular member 37, the uneven temperature distribution in hollow tubular member 36 can be suppressed.

Since sample gas should be sealed in the inside of hollow tubular member 36, hollow tubular member 36 should be connected to holding members 33 and 34 while airtightness is ensured. In the inside of hollow tubular member 37, on the other hand, sample gas does not have to be sealed, and hence hollow tubular member 37 should only be provided as far as the vicinity of holding members 33 and 34 that hold mirrors 31 and 32 and does not have to be connected to holding members 33 and 34. Therefore, the bellows to serve as the thermal resistance does not have to be provided in hollow tubular member 37 as in hollow tubular member 36.

As set forth above, gas measurement apparatus 100 according to the present embodiment includes optical resonator 3 that resonates light, light source 1 that generates light for irradiation of optical resonator 3, and photodetector 6 that detects light taken out of optical resonator 3. Optical resonator 3 includes a plurality of mirrors 31 and 32, holding members 33 and 34 that hold the plurality of mirrors 31 and 32, respectively, hollow tubular member 36 including the opposing ends in contact with holding members 33 and 34, hollow tubular member 36 defining a space where the plurality of mirrors 31 and 32 are accommodated, hollow tubular member 37 provided in the inside of hollow tubular member 36 along hollow tubular member 36, and temperature adjustment instrument 38 that adjusts the temperature in the inside of hollow tubular member 36. Holding members 33 and 34 are composed of a material lower in thermal expansion coefficient than hollow tubular member 36. Hollow tubular member 36 includes the portion (first portion) composed of a material higher in thermal conductivity than holding members 33 and 34 and bellows 36a and 36b (second portion) higher in elasticity than the portion. Hollow tubular member 37 is composed of a material equal to or higher than hollow tubular member 36 in thermal conductivity and provided as far as the positions of the plurality of mirrors 31 and 32 on the inner side of bellows 36a and 36b. Optical resonator 3 according to the present embodiment can thus achieve heating or cooling to a target temperature with the uneven temperature distribution caused in the inside of hollow tubular member 37 being suppressed while optical stability is ensured with holding members 33 and 34 fixing the positions of mirrors 31 and 32.

Bellows 36a and 36b can keep the distance (resonator length L1) between mirror 31 and mirror 32 constant by being provided at at least one end of hollow tubular member 36, and the distance can be kept by fixing of relative positions of holding members 33 and 34 in the shape of the flange that hold mirrors 31 and 32 by fixing of holding members 33 and 34 by at least three rods 35 (fixing portion).

Figure 4:
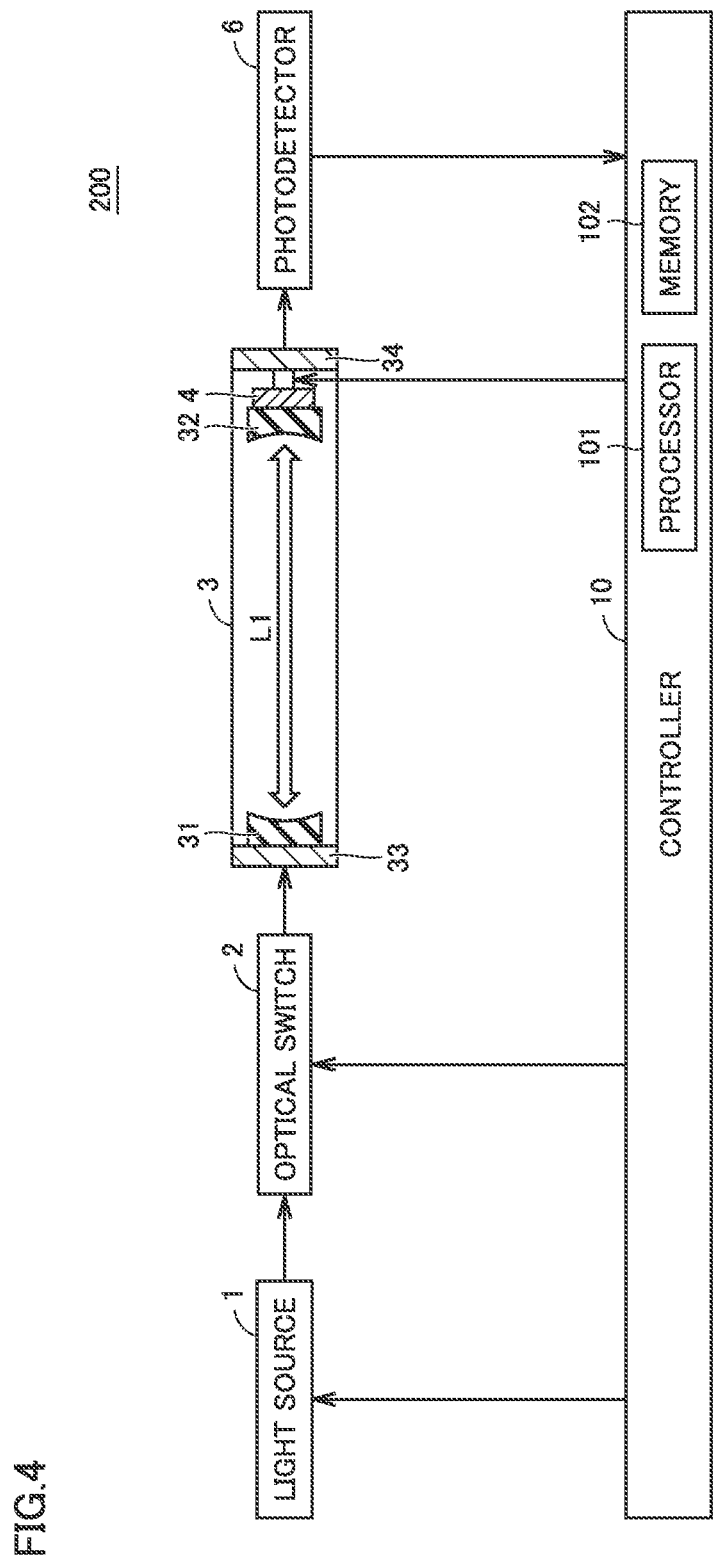
FIG. 4 is a block diagram showing an overall configuration of a gas measurement apparatus according to a modification.

Modification (1) FIG. 4 is a block diagram showing an overall configuration of a gas measurement apparatus 200 according to a modification. Gas measurement apparatus 200 shown in FIG. 4 is different from gas measurement apparatus 100 (see FIG. 1) according to the embodiment in that an optical switch 2 is provided between light source 1 and optical resonator 3 and a piezo element 4 that displaces mirror 32 is provided in holding member 34. In other words, gas measurement apparatus 200 can change resonator length L1 by displacing mirror 32.

Optical switch 2 switches between emission and cut-off of laser beams from light source 1 to optical resonator 3 in accordance with an instruction from controller 10. For example, an acousto-optic modulator (AOM) can be adopted as optical switch 2. Optical switch 2 cuts off laser beams emitted to optical resonator 3 after power of laser beams from light source 1 is sufficiently stored in optical resonator 3.

In piezo element 4, a hole for passage of light is provided like a doughnut and piezo element 4 displaces mirror 32 in the direction of the optical axis. Controller 10 can control piezo element 4 to displace mirror 32 to thereby change resonator length L1. Controller 10 has mirror 32 swept such that resonator length L1 changes by a prescribed amount. The piezo element may be provided in holding member 33 on the side of mirror 31 so as to displace mirror 31 in the direction of the optical axis. A feature that displaces mirror 32 is not limited to piezo element 4, and any actuator capable of displacing the mirror in the direction of the optical axis may be applicable.

As set forth above, in gas measurement apparatus 200 according to the modification, holding member 34 includes piezo element 4 that displaces mirror 32 held thereby. Gas measurement apparatus 200 can thus conduct measurement with resonator length L1 being varied by a prescribed amount.

(2) FIG. 5 is a block diagram showing an overall configuration of a gas measurement apparatus 300 according to another modification. Gas measurement apparatus 300 shown in FIG. 5 is different from gas measurement apparatus 100 according to the embodiment (see FIG. 1) in that a ring-shaped optical resonator including three mirrors is adopted rather than a Fabry-Perot optical resonator including two mirrors.

An optical resonator 8 includes three mirrors 81 to 83 arranged in the inside. Laser beams emitted to optical resonator 8 repeat reflection in the order of mirror 81, mirror 82, mirror 83, mirror 81, mirror 82, mirror 83, . . . . Mirrors 81 and 82 are plane mirrors. Mirror 83 is a concave mirror. A distance between mirror 81 and mirror 83 is equal to a distance between mirror 83 and mirror 82. This distance is denoted as a "resonator length L2."

Mirror 83 is provided with a piezo element 9. Piezo element 9 displaces mirror 83 in accordance with an instruction from controller 10. Resonator length L2 can thus be changed. When mirror 83 does not have to be displaced, mirror 83 does not have to be provided with piezo element 9.

Though not shown, holding members that hold mirrors 81 to 83 and rods that fix positions of the holding members are composed of a material (for example, an Invar® alloy or ultra-low-expansion glass) low in thermal expansion coefficient. The hollow tubular member (first tubular portion) that defines the space where mirrors 81 to 83 are accommodated is composed of a material (for example, aluminum, copper, or the like) high in thermal conductivity. The hollow tubular member (first tubular portion) includes the bellows, and the hollow tubular member (second tubular portion) equal to or higher than the hollow tubular member (first tubular portion) in thermal conductivity is further provided in the inside thereof.

(3) The Fabry-Perot optical resonator is explained in the embodiment described previously. A Herriott cell (multi reflection cell) composed of at least two mirrors, however, may be adopted as the optical resonator.

(4) Use of hollow tubular members 36 and 37 for optical resonator 3 is explained in the embodiment described previously. The optical resonator, however, is not limited to hollow tubular members 36 and 37 in a columnar shape. So long as the optical resonator is in a tubular shape, a tubular member in a prismatic shape such as a triangular prism or a quadrangular prism may be adopted.

(5) According to the embodiment described previously, bellows 36a and 36b are provided to cancel or lessen deformation of hollow tubular member 36. Optical resonator 3, however, is not limited to the configuration where the bellows is provided in hollow tubular member 36, and a highly elastic member (for example, a resin, rubber, or the like) may be adopted instead of the bellows. According to the embodiment described previously, rod 35 is adopted as the fixing portion that fixes the positions of holding members 33 and 34. The fixing portion, however, is not limited to rod 35. So long as the positions of holding members 33 and 34 can be fixed, a plate member or a part of another apparatus may be adopted, and when holding members 33 and 34 are fixed to the gas measurement apparatus itself, the fixing portion itself does not have to be provided.

Aspects

The embodiment described above is understood by a person skilled in the art as specific examples of aspects below.

Clause 1

A measurement apparatus according to one aspect includes an optical resonator that resonates light, a light source that generates light for irradiation of the optical resonator, and a photodetector that detects light taken out of the optical resonator, the optical resonator includes a plurality of mirrors, a holder that holds the plurality of mirrors, a first tubular portion including opposing ends in contact with the holder, the first tubular portion defining a space where the plurality of mirrors are accommodated, a second tubular portion provided in the inside of the first tubular portion along the first tubular portion, and a temperature adjustment portion that adjusts a temperature in the inside of the first tubular portion, the holder is composed of a material lower in thermal expansion coefficient than the first tubular portion, the first tubular portion includes a first portion composed of a material higher in thermal conductivity than the holder and a second portion higher in elasticity than the first portion, and the second tubular portion is composed of a material equal to or higher than the first portion in thermal conductivity and provided as far as positions of the plurality of mirrors on an inner side of the second portion.

According to the measurement apparatus described in Clause 1, the holder lower in thermal expansion coefficient than the first tubular portion holds the plurality of mirrors and the second tubular portion equal to or higher than the first portion in thermal conductivity is provided as far as the positions of the plurality of mirrors on the inner side of the second portion. Therefore, heating or cooling to a target temperature can be performed with an uneven temperature distribution caused in the inside being suppressed while optical stability is ensured. According to the measurement apparatus described in Clause 1, a temperature in the optical resonator can be controlled to obtain high detection sensitivity.

Clause 2

In the measurement apparatus described in Clause 1, the second portion is provided at at least one end of the first tubular portion. According to the measurement apparatus described in Clause 2, deformation caused in the first portion high in thermal conductivity can be cancelled or lessened.

Clause 3

In the measurement apparatus described in Clause 1 or 2, a bellows is provided as the second portion. According to the measurement apparatus described in Clause 3, deformation caused in the first portion high in thermal conductivity can be cancelled or lessened.

Clause 4

In the measurement apparatus described in any one of Clauses 1 to 3, the holder includes a plurality of holding members that hold the plurality of mirrors, respectively, and the measurement apparatus further includes a fixing portion that fixes a relative position of each holder. According to the measurement apparatus described in Clause 4, the fixing portion can fix the relative position of the holder to thereby keep the distance between the mirrors constant.

Clause 5

In the measurement apparatus described in Clause 4, the plurality of mirrors include a first mirror and a second mirror, the holder includes, at least, a first holder that holds the first mirror and a second holder that holds the second mirror, and the fixing portion keeps a distance between the first holder and the second holder constant.

According to the measurement apparatus described in Clause 5, even when the temperature adjustment portion adjusts the temperature, the distance between the first mirror and the second mirror can be kept constant.

Clause 6

In the measurement apparatus described in Clause 5, the fixing portion is made up of at least three rods that fix the first holder and the second holder each in a shape of a flange, and the rods are composed of a material lower in thermal expansion coefficient than the first tubular portion.

According to the measurement apparatus described in Clause 6, the distance between the first mirror and the second mirror can be kept constant while manufacturing cost is lowered.

Clause 7

In the measurement apparatus described in any one of Clauses 1 to 6, the holder includes a piezo element that displaces a mirror held by the holder. According to the measurement apparatus described in Clause 7, the mirror can be displaced to change a resonator length.

Though an embodiment of the present invention has been described, it should be understood that the embodiment disclosed herein is illustrative and non-restrictive in every respect. The scope of the present invention is defined by the terms of the claims and is intended to include any modifications within the scope and meaning equivalent to the terms of the claims.

What is claimed is:
1. A measurement apparatus comprising:
   an optical resonator that resonates light;
   a light source that generates light for irradiation of the optical resonator; and
   a photodetector that detects light taken out of the optical resonator, wherein
   the optical resonator includes
      a plurality of mirrors,
      a holder that holds the plurality of mirrors,
      a first tubular portion including opposing ends in contact with the holder, the first tubular portion defining a space where the plurality of mirrors are accommodated,
      a second tubular portion provided inside of the first tubular portion along the first tubular portion, and
      a temperature adjustment portion that adjusts a temperature in the inside of the first tubular portion,
   the holder is composed of a material lower in thermal expansion coefficient than the first tubular portion,
   the first tubular portion includes
      a first portion composed of a material higher in thermal conductivity than the holder, and
      a second portion higher in elasticity than the first portion, and
   the second tubular portion is composed of a material equal to or higher than the first portion in thermal conductivity and provided as far as positions of the plurality of mirrors on an inner side of the second portion.
2. The measurement apparatus according to claim 1, wherein
   the second portion is provided at at least one end of the first tubular portion.
3. The measurement apparatus according to claim 1, wherein
   a bellows is provided as the second portion.
4. The measurement apparatus according to claim 1, wherein
   the holder includes a plurality of holding members that hold the plurality of mirrors, respectively, and
   the measurement apparatus further comprises a fixing portion that fixes a relative position of each holder.
5. The measurement apparatus according to claim 4, wherein
   the plurality of mirrors include a first mirror and a second mirror, the holder includes, at least, a first holder that holds the first mirror and a second holder that holds the second mirror, and the fixing portion keeps a distance between the first holder and the second holder constant.

6. The measurement apparatus according to claim 5, wherein the fixing portion is made up of at least three rods that fix the first holder and the second holder each in a shape of a flange, and the rods are composed of a material lower in thermal expansion coefficient than the first tubular portion.

7. The measurement apparatus according to claim 1, wherein the holder includes a piezo element that displaces a mirror held by the holder.

* * * * *